United States Patent [19]

Dubut et al.

[11] Patent Number: 5,044,370

[45] Date of Patent: Sep. 3, 1991

[54] PROBE WITH BAR OF PIEZOELECTRIC ELEMENTS FOR ULTRASOUND APPARATUS

[75] Inventors: Patrick Dubut, Tourrettes S/Loup; Jean-Francois Gelly, Valbonne, both of France

[73] Assignee: General Electric CGR, Issy les Moulineaux, France

[21] Appl. No.: 368,364

[22] PCT Filed: Nov. 24, 1987

[86] PCT No.: PCT/FR87/00465

§ 371 Date: May 24, 1989

§ 102(e) Date: May 24, 1989

[87] PCT Pub. No.: WO88/04092

PCT Pub. Date: Jun. 2, 1988

[30] Foreign Application Priority Data

Nov. 28, 1986 [FR] France ................................ 88 16663

[51] Int. Cl.[5] .......................... A61B 8/00; H01L 41/22

[52] U.S. Cl. .............................. 128/662.03; 29/25.35; 310/336

[58] Field of Search ....................... 128/661.09, 661.10; 73/675, 626; 29/25.35

[56] References Cited

U.S. PATENT DOCUMENTS

| | | | |
|---|---|---|---|
| 4,217,684 | 8/1980 | Brisken et al. | 29/25.35 |
| 4,747,192 | 5/1988 | Rokurota | 29/25.35 |
| 4,894,895 | 1/1990 | Rokurohta et al. | 29/25.35 |

*Primary Examiner*—Francis Jaworski

*Attorney, Agent, or Firm*—Oblon, Spivak, McClelland, Maier & Neustadt

[57] ABSTRACT

The electric connection between the control circuits (13,14) of a probe and the metallized faces (5,6) of the piezoelectric elements (2) of said probe is provided by metallizations (6,8) made on parts, support (1) or blade (4) in contact with said metallized faces. The mechanical and electric connection between said metallizations may be provided by a thin layer of conducting glue (19,20).

9 Claims, 1 Drawing Sheet

PROBE WITH BAR OF PIEZOELECTRIC ELEMENTS FOR ULTRASOUND APPARATUS

BACKGROUND AND SUMMARY OF THE INVENTION

An object of the present invention is an probe with a bar of piezoelectric elements for an ultrasound apparatus. It finds application more particularly in the medical field where echographic ultrasound apparatuses are used for diagnostic purposes to show internal tissue structures of human bodies examined. However, it can be implemented in other field once a problem of electrical connection has to be resolved between a piezoelectric element and the control circuits of a probe to which it belongs.

An echograph has, schematically, a generator of electrical signals and a transducer probe to apply a mechanical vibration corresponding to these signals in a medium to be examined. During stops in transmission, the probe may be used reversibly to receive acoustic signals back-reflected by the medium, and to convert these signals into electrical signals which are subsequently applied to reception and processing means. For various reasons, notably for questions of resolution of the image restored by an echograph, the frequency of the electrical-acoustic signal is high. For these same reasons, the probe consists of several transducer elements aligned with one another. Each transducer piezoelectric element has two metallizations, which are located on opposite faces of this element and which must be connected to the transmission-reception circuits of the echograph. The dimensions of these elements are small and cause difficulties in making the system of connection of the electrical signal to these elements.

It is known, notably from a European patent application No. 84 308 373.4 filed on 3rd December 1984, that the electrical signal can be applied or picked up at the terminals of each transducer element in soldering electrical connection tracks, supported by a flexible printed circuit, directly to the metallizations of the elements. Subsequently, the flexible printed circuits are folded towards the rear of the probe and, by various arrangements, the probe is furthermore curved to correspond to a particularly desired use for the exploration of the medium studied: by sector scanning. This solution has numerous drawbacks. For example, the electrical connections are distributed at hot points on one side of the bar and cold points on the other side. This increases problems of diaphony among elements in this bar. Furthermore, the elements are metallized on three of their contiguous surfaces, and two electrically independent metallizations, assigned to the two faces of the element, have to be prepared by making a saw mark in the piezoelectric crystal thus prepared. This saw mark is difficult. It was conceived to overcome these drawbacks by adding, to either side of the transducer element, a relay block continuously metallized on at least two of its adjacent faces. The relay block can then be electrically connected by one of its faces to one of the faces of the transducer element and by its other face to a printed circuit type of connection circuit. For this printed circuit, the problems of curvature of the bar no longer play a role since its connections can be made after the curvature of this bar.

An example of an embodiment of this type is shown in FIG. 1. It was then thought to connect the corresponding faces of the relay blocks and the elements by connecting wires. This micro-connection operation is, however, difficult to undertake. In the present invention, advantage has been taken of the fact that the piezoelectrical elements are covered with a transition blade. This blade enables the acoustic signal to be adapted to the medium to be studied. This blade has the specific feature herein of being metallized on its face which is before the piezoelectric element that it covers. Besides, this blade goes beyond the piezoelectric element and also covers the relay block used for the electrical connection. The electrical signals are then conducted simply from the printed circuit, to the relay block, to the metallization of the blade and then finally to the metallization of the piezoelectric element.

In one improvement of the invention, a layer of non-conductive bonder is used to ensure the mechanical-electrical continuity among the support, the element and the blade. Contrary to what might have been expected, the layer of non-conductive bonder does not form an insulating screen for the electrical connection. In effect, non-conductive bonders have the particular feature of being very fluid. They can therefore be used in very small thickness. In then using faults in the appearance of the metallizations, which give these metallizations a granulated appearance, it is possible, by exerting adequate pressure during the bonding of the parts by their metallized part, to obtain a hammering, a molecular interpretation between these metallization layers. In this way, the bonding between these layers may be considered to be a dispersal of a multitude of electrical bridges between the mechanical bonds caused by the presence of the bonder. In any case, bonding of the metallizations, by bonder which is conductive or not, has the advantage over solders of not causing any additional risk of loosening of these metallizations.

The invention therefore concerns a probe for an ultrasound apparatus of the type with a bar of piezoelectric elements, each element being inserted between a support and an acoustic transition blade and being metallized on its faces which are before the support and its blade, characterized in that the blade and/or the support include a facing metallization designed to be connected to the corresponding metallization of the element.

BRIEF DESCRIPTION OF THE DRAWINGS

The invention will be better understood from the reading of following description and from the examination of the accompanying figures. They are given purely by way of indication and in no way restrict the scope of the invention. The figures show.

DETAILED DESCRIPTION OF THE PREFERRED EMBODIMENTS

Figure 1:
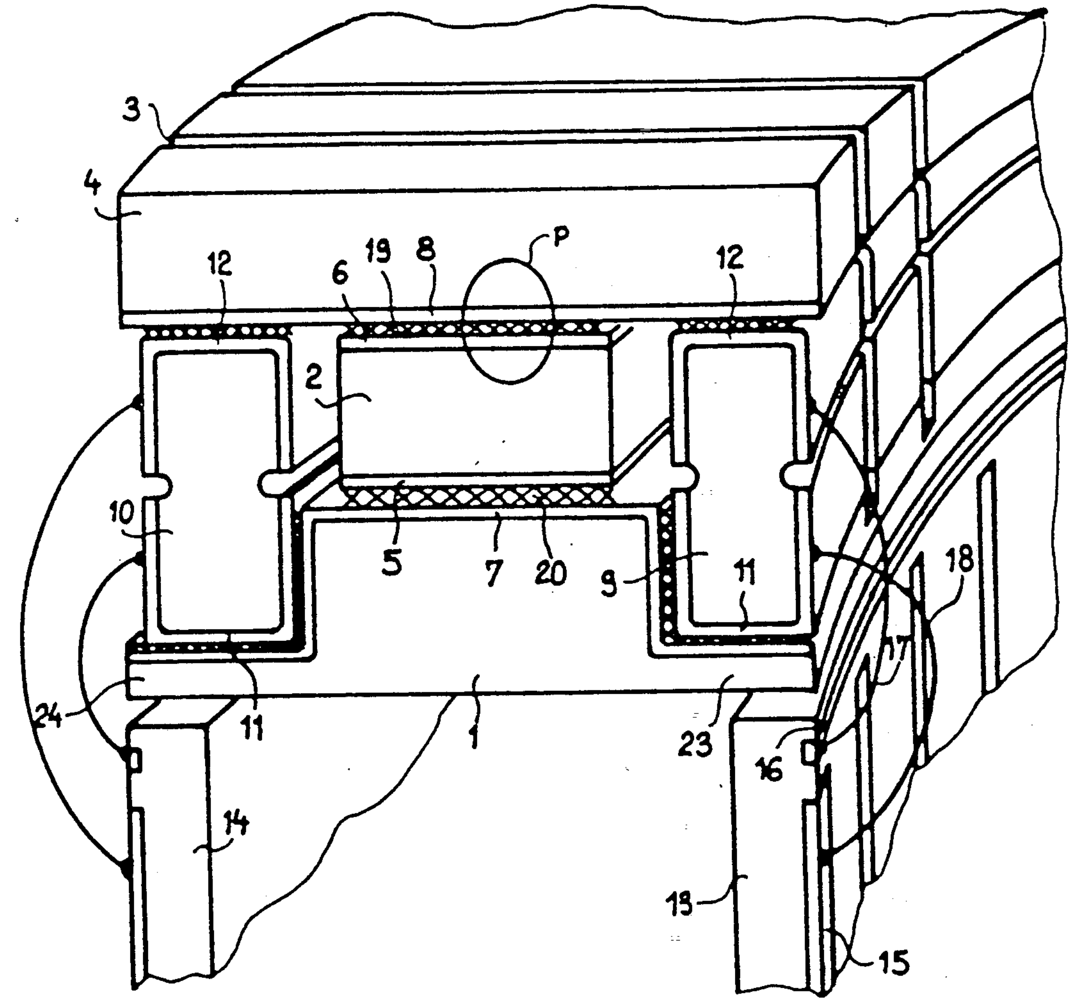
FIG. 1: a view in perspective of an ultrasound probe apparatus according to the invention.

FIG. 1 shows a part of an ultrasound apparatus probe with a bar of piezoelectric elements according to the invention. This probe has a support 1 common to several transducer elements such as 2. The transducer elements are separated from one another by separations such as 3. Each element is covered by a blade 4 called an acoustic transition blade and has, on its faces before the support and the blade, a metallization 5 and 6 respectively. In the invention, the support and the blade also have metallizations 7 and 8 respectively. These metallizations are designed to be connected to the metallizations of the elements. In a preferred exemplary embodiment, the device for the electrical connection of the elements has, on either side of each element, a parallelepiped relay block such as 9 or 10. The blocks are made of an insulating material, for example of a ceramic. They are metallized on their surface by two electrically independent metallizations and 12 respectively, each time. The various metallizations are obtained simply, for example, vacuum evaporation-spraying, electrolysis or other methods. The electrical signals are conducted between the electronic circuits of the probe (not shown) and the piezoelectric elements, by printed circuits such as 13 and 14, the tracks 15 or 16 of which are connected by connections 17, 18 to the electrically independent metallized lateral faces of the blocks 9 and 10. The connection of the connections is obtained, for example, by thermocompression of the ends of the wires 17 and 18. This thermocompression cannot cause damage in the metallizations of the support, the element or its blade because these parts are only bonded to one another.

Figure 2:
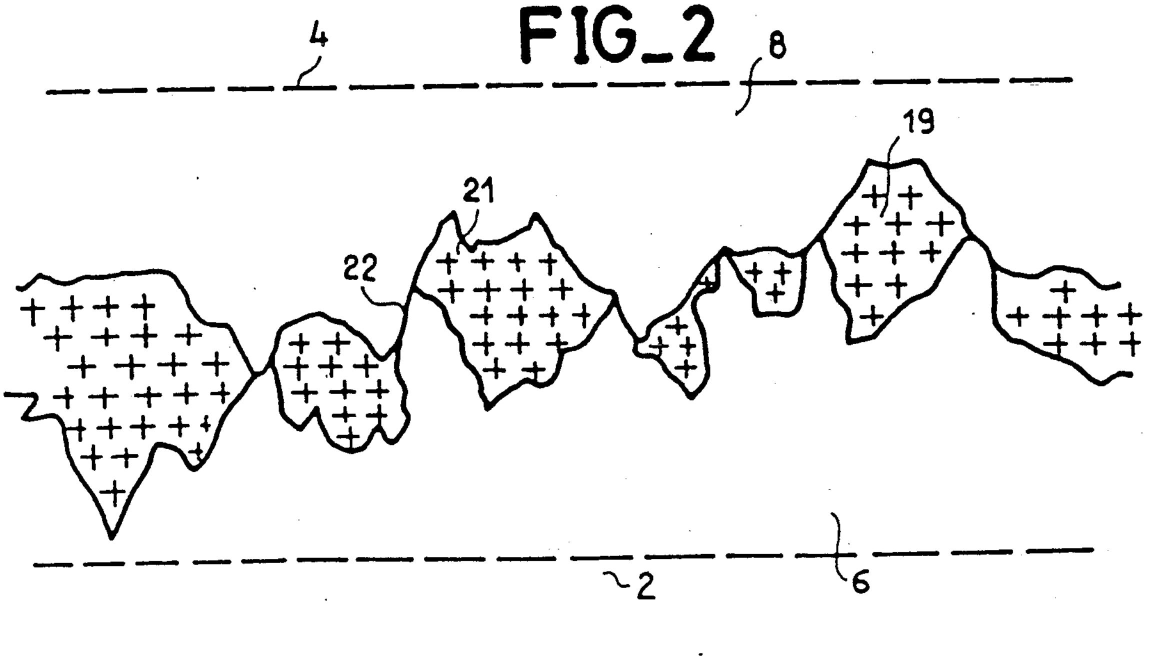
FIG. 2: a section of a detail of a part of FIG. 1 giving a schematic view of the electrical continuity.

By way of an improvement in the invention, we might note the presence, to conduct the electrical signals between the metallizations 6 and 7, on the one hand, and/or between the metallizations 5 and 7, on the other hand, of layers 19 and 20 respectively of non-conductive bonder. FIG. 2 is an enlargement of a part P of the connection between the upper face of a piezoelectric element and the lower face of the transition blade which covers it. It shows that the metallizations 6 and 8 respectively of these two parts are not perfectly smooth. On the contrary, they show microscopic points of roughness. A layer of non-conductive bonder 19 is then spread before assembling these parts. Then, a sufficient pressure, for example of the order of 50 kg per cm2, is exerted and the highly fluid bonder escapes on the sides of the bonding. It leaves in position only tiny mechanical bonds 21 among which there is dispersed a multitude of electrical bridges 22. In these conditions, the electrical connection is efficient between the metallization 8 and the metallization 6 and the acoustic coupling between the element 2 and its blade 4 is direct. The same operation can be done for the support.

A bar of piezoelectric elements is fabricated as follows: on an elongated support 1 in the shape of an upside-down T, previously metallized on its upper face, there is placed, in a preferred way, with a layer of non-conductive bonder, a bar of a piezoelectric material metallized on both its faces. Then, on the two wings 23 and 24 of the support, strips are placed, comprising two electrically independent metallizations: here again, by preference, in using an interposed layer of non-conductive bonder. Finally, with a non-conductive bonder, a blade of the same length as the support, the piezoelectric and the strips, is bonded on top of the entire unit. The unit is subjected to sufficient pressure and the bonder is allowed to set. When the setting is over, cuts 3 are made, for example with a saw, to separate the bar into many independent elements. The cuts are not entire cuts, the support remains common to the entire element. To form a curved bar, it then suffices to curve the support 1 in the desired shape. In a preferred way, the support is a thermoformable material, and the curvature is obtained during a heating-cooling cycle.

The invention further provides an unexpected advantage. The use of non-conductive bonder enables the elimination of any risks of short-circuits between the different metallizations. These short-circuits may be due, in the prior art referred to, to the use of conductive bonders which spread all over. The result thereof is that the efficiency of fabrication of the probes can be considerably increased herein. In a preferred way, the non-conductive bonder is a structural bonder, hence with very high adhesive capacity and, in addition, it is a so-called high-temperature bonder, i.e. highly stable at low temperature or at ambient temperature but highly fluid at its (high) temperature of application. However, it is not necessary to make all the electrical connections of the elements of the bar with non-conductive bonder. In particular, the connections between the metallization 5 of an element and the metallization 7 of the support should not necessarily be made with a layer of non-conductive bonder. At this place, in effect, stray reflections of acoustic vibrations are less worrying because they occur in a non-useful direction: towards the rear of the bar. They are therefore less troublesome.

We claim:

1. An ultrasonic probe comprising: a bar of piezoelectric transducer elements, each element emitting an acoustic wave along a propagating path, being inserted between a support and an acoustic transition blade and having a metallization on respective faces thereof which are juxtaposed to the support and the blade, wherein at least one of the blade and the support includes a facing metallization for electrical connection to the corresponding metallization of the element to form an electrical contact positioned to prevent interference with the propagating path of the acoustic wave.

2. A probe according to claim 1, wherein the support is common to all the elements.

3. A probe according to claim 1, wherein the connection of the metallizations is obtained by bonding.

4. A probe according to claim 1, wherein the blade and the support extend laterally adjacent to the elements and enclose, at each element, at least one electrical connection relay.

5. A probe according to claim 4, wherein the relay includes a parallelepiped element provided with at least one continuous metallization made on at least two of its contiguous faces for contacting the metallization of one of the blade and the support.

6. A probe according to claim 5, wherein the parallelepiped element is bonded by its metallization with a bonder to the metallization of one of the support and the blade.

7. A probe according to any one of the claims 2 to 6 wherein the support is thermodeformable and is thermodeformed to form a curved bar.

8. A probe according to claim 1, wherein a thin layer of non-conductive bonder is interposed between the corresponding metallizations of the support, of the element and of the blade to ensure electrical continuity.

9. A probe according to claim 8, wherein the corresponding metallizations to be bonded comprise a surface appearance which is favourable to their mutual molecular interpenetration.

* * * * *